United States Patent
Te Lintel Hekkert et al.

(10) Patent No.: US 6,594,016 B1
(45) Date of Patent: Jul. 15, 2003

(54) METHOD OF SPECTROSCOPICALLY DETERMINING A VOLATILE ORGANIC COMPOUND IN A GAS GIVEN OFF BY A MAMMAL

(75) Inventors: Sacco Te Lintel Hekkert, Nijmegen (NL); Franciscus Johannes Maria Harren, Nijmegen (NL); David Hubert Parker, Nijmegen (NL)

(73) Assignee: Stichting voor de Technische Wetenschappen, Utrecht (NL)

( * ) Notice: Subject to any disclaimer, the term of this patent is extended or adjusted under 35 U.S.C. 154(b) by 0 days.

(21) Appl. No.: 09/582,980

(22) PCT Filed: Jan. 7, 1999

(86) PCT No.: PCT/NL99/00004

§ 371 (c)(1),
(2), (4) Date: Sep. 5, 2000

(87) PCT Pub. No.: WO99/35484

PCT Pub. Date: Jul. 15, 1999

(30) Foreign Application Priority Data

Jan. 7, 1998 (NL) .............................................. 1007970

(51) Int. Cl.[7] .............................................. G01N 21/61
(52) U.S. Cl. .................... 356/437; 600/532; 73/23.3
(58) Field of Search ................................. 600/310, 473, 600/306, 529, 532; 250/341.1; 356/432, 437, 438, 439; 73/23.3, 24.01, 24.02, 24.06, 31.03; 436/900

(56) References Cited

U.S. PATENT DOCUMENTS 5,125,749 A * 6/1992 Leugers et al. ............. 356/432
5,900,533 A * 5/1999 Chou ..................... 250/339.13

FOREIGN PATENT DOCUMENTS

| EP | 0557658 A1 | 9/1993 |
|---|---|---|
| EP | 0757242 A2 | 2/1997 |
| GB | 1509174 | 4/1978 |
| WO | WO81/02632 | 9/1981 |

OTHER PUBLICATIONS

Kneepkens, et al., Free Radical Biology & Medicine, vol. 17, No. 2, pp. 127–160 (Jan. 4, 1994).*
Bijnen, F.G.C., et al., "Geometrical Optimization of a Longitudinal Resonant Photoacoustic Cell for Sensitive and Fast Trace Gas Detection," *Rev. Sci. Instrum.*, vol. 67, No. 8 Aug. 1996).
Phillips, M., "Breath Tests in Medicine," *Scientific American*, pp 32–37 (Jul. 1992).
Bijnen, F.G.C., et al., "Intracavity CO Laser Photoacoustic Trace Gas Detection: Cyclic $CH_4, H_2O$ and $CO_2$ Emission by cockroaches and Scarab Beetles" *Applied Optics*, vol. 35, No. 27, pp. 5357–5368 (Sep. 20, 1996).
Kneepkens, C.M.F., et al., "The Potential of the Hydrocarbon Breath Test as a Measure of Lipid Peroxidation," *Free Radical Biology and Medicine*, vol. 17, No. 2, pp. 127–160 (1994).

* cited by examiner

Primary Examiner—Richard A. Rosenberger
Assistant Examiner—Vincent P. Barth
(74) Attorney, Agent, or Firm—Jeffrey D. Myers

(57) ABSTRACT

The invention relates to a method of spectroscopically determining the concentration of a volatile organic compound in a gas given off by a mammal. According to the invention, the spectroscopic technique applied is photoacoustic spectroscopy and the strength of the acoustic effect is determined by means of a microphone, as being the measure of the concentration of the organic compound.

18 Claims, 3 Drawing Sheets

Figure 1:
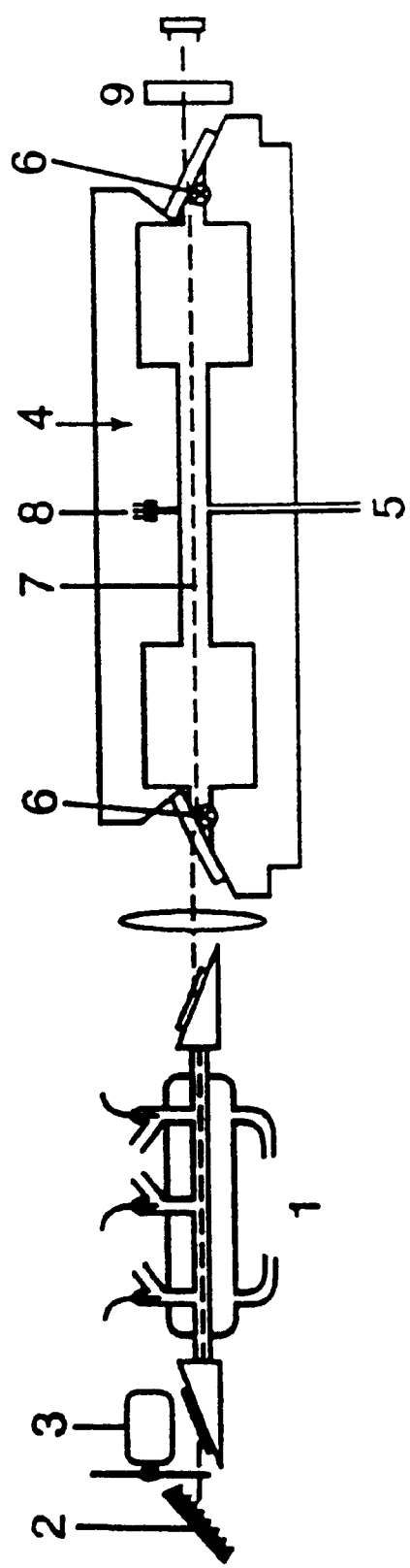

METHOD OF SPECTROSCOPICALLY DETERMINING A VOLATILE ORGANIC COMPOUND IN A GAS GIVEN OFF BY A MAMMAL

The present invention relates to a method of measuring the effect of a compound on a mammal by measuring the concentration of an organic compound spectroscopically.

Methods of spectroscopically determining the effect of a compound are generally known. As a general example, it is known to administer a compound to a mammal and measure, for example using an ELISA, a second compound as a measure of the physiological effect of the first compound on the mammal.

The object of the present invention is to make it possible to perform sensitive measurements. An additional goal is to make it possible to measure continuously so that fluctuations in the concentration occurring within a short period of time, as a result of the effect of the compound on the mammal, can be detected.

To this end the present invention is characterized in that the organic compound is a volatile organic compound, the concentration of which is measured in a gas given off by the mammal using photoacoustic spectroscopy, the volatile organic compound not being the compound or a degradation product thereof.

Photoacoustic spectroscopy is a spectroscopic technique that makes it possible to perform sensitive measurements without a concentration step. It also makes it possible to measure continuously so that fluctuations in the concentration occurring within a short period of time, can be detected, for example in the breath of the mammal.

Both photoacoustic spectroscopy and breath analysis have been known for some time. But even a very recent review article by Kneepkens, C. M. F. et al. (ref. 2) makes no mention of photoacoustic spectroscopy and its possibilities for measuring the effect of a compound. The same applies to EP 0 757 242 which discloses the use of photoacoustic spectroscopy for detecting the metabolization of a labelled compound, the degradation product thereof being measured.

When mention is made in the present application of a compound to be tested for its effect on a mammal, a compound is meant which is not a tracer. In other words, it is not the compound itself nor one of its decomposition products whose concentration is being measured by the method according to the invention. What is being examined is the physiological effect of the compound on the organism including the compound's protective effect against a stress factor.

According to one embodiment, the mammal is subjected to a factor that changes the concentration of the volatile organic compound in the breath.

Thanks to the fact that with the method according to the invention measuring can be performed continuously, the invention makes it possible to expose the mammal, for example a human, to a stimulus and to determine the effect of the concentration of the volatile organic compound to be measured.

According to a preferred embodiment the factor is a stress factor, in particular UV radiation.

Surprisingly it has been shown that UV radiation influences the composition of breath and that this change can be measured. This opens possibilities for testing products for the protection of skin against UV radiation.

According to a very favourable embodiment the compound is one to be tested for the presence of a pharmaceutical characteristic. For instance, it could be possible to quickly and non-invasively examine the restoring capacity for containing the consequences of a myocardial infarct.

According to a favourable embodiment the measured concentration is normalized. Preferably this is done by using at least one parameter selected from the group comprising weight, lung capacity (measure of lung surface area), respiratory volume (l/min), volume of each breath, blood flow rate, the concentration of a further compound selected from the group comprising a marker gas, carbon dioxide, oxygen; and the mammal's percentage of fat.

In this manner diagnosing can be facilitated or made more reliable, based on the detection of one or more further compounds. As marker gas it is possible to use, for example, $SF_6$.

The volatile organic compound is preferably a hydrocarbon composition with the general formula $C_xH_y$, x and y being integers, $x \leq 10$ en $y \geq x$ is.

Such hydrocarbon compounds can be used for numerous diagnoses.

According to a preferred embodiment the hydrocarbon compound is an unsaturated hydrocarbon compound, in particular ethene.

Ethene was shown to be present in the breath of humans, and to be useful, among other things, for examining the effect of UV radiation on humans.

According to a favourable embodiment a housing which is open at one side and provided with an inlet for a carrier gas, is placed against a portion of a mammal's surface, said portion not comprising an open body orifice, the carrier gas is fed through the housing, and the carrier gas containing the gas given off by the mammal is led away via an outlet in the housing and is subsequently measured photoacoustically.

The surface of the mammal may be any surface that cannot be reached via surgery, and in particular one where blood vessels are close to the surface such as, for instance, the inside of the mouth. Particularly suitable is the skin which is easily accessible and of which a large area can be used, if necessary. The advantage of this embodiment is that it avoids problems arising from the high flow rate of breathing air and the variable composition of one breath, resulting from the fact that the lung's inlet opening for oxygen is the same as the outlet opening. In addition, it becomes easier to normalize concentrations, for example, on the basis of the carbon dioxide that is also given off. Moreover, if desired, the concentration of the compound may be brought into a convenient measuring range by adjusting the flow rate of the carrier gas, by treating the respective portion of the body surface with permeabilizing agents, and/or by suitably dimensioning the surface of the housing covered by the open side. optionally an underpressure may be applied, which promotes blood circulation and the release of gas, or an overpressure, which is a simple manner of avoiding pollutants from the surroundings coming into the gas to be analyzed. Also, the mammal's comfort is not lessened, as may be the case when the breathing is measured. This is in particular the case with patients, such as cardiac patients, who are in a precarious, non-stable condition, and who could be harmed by measurements being performed.

Figure 2:
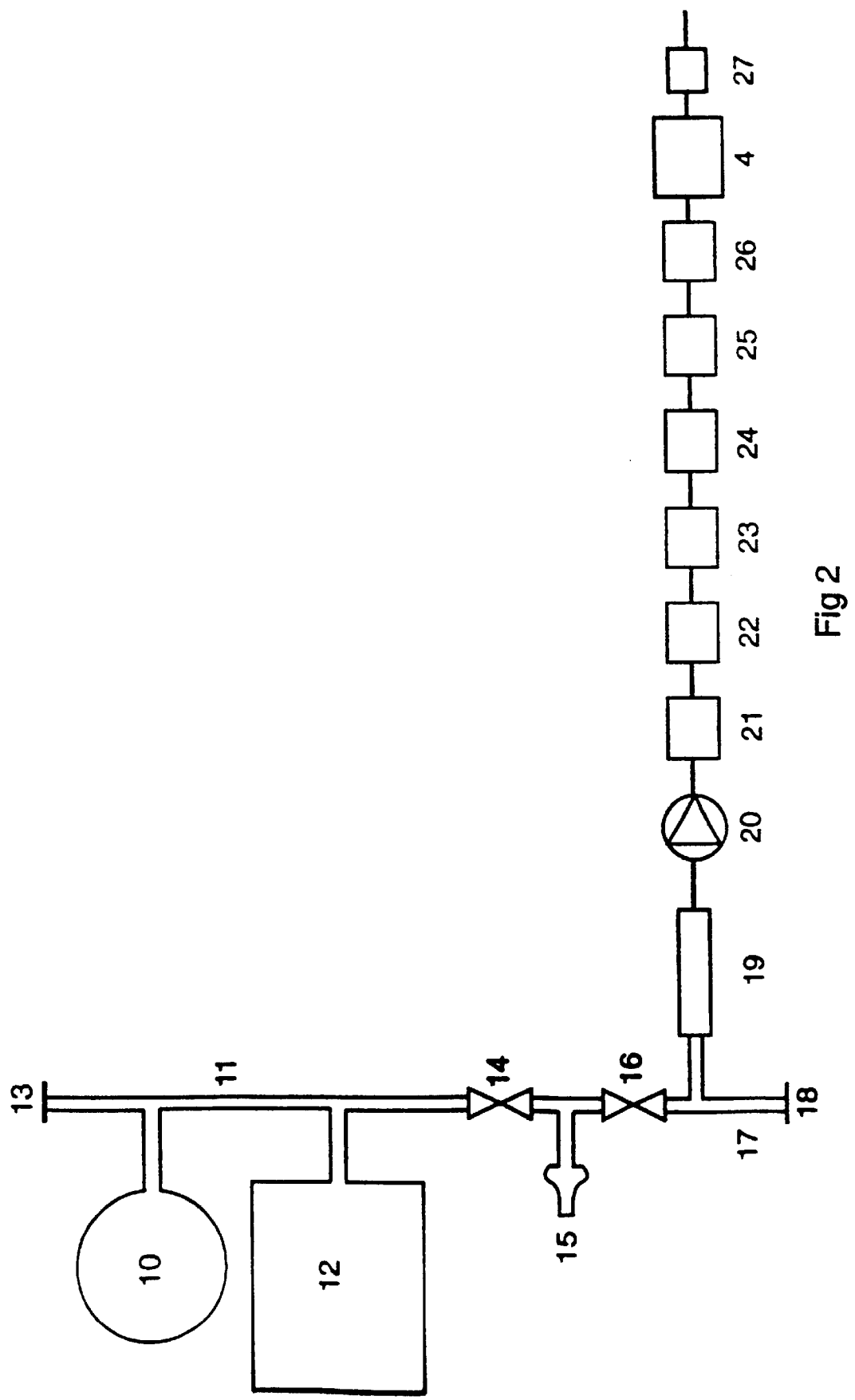
Figure 3:
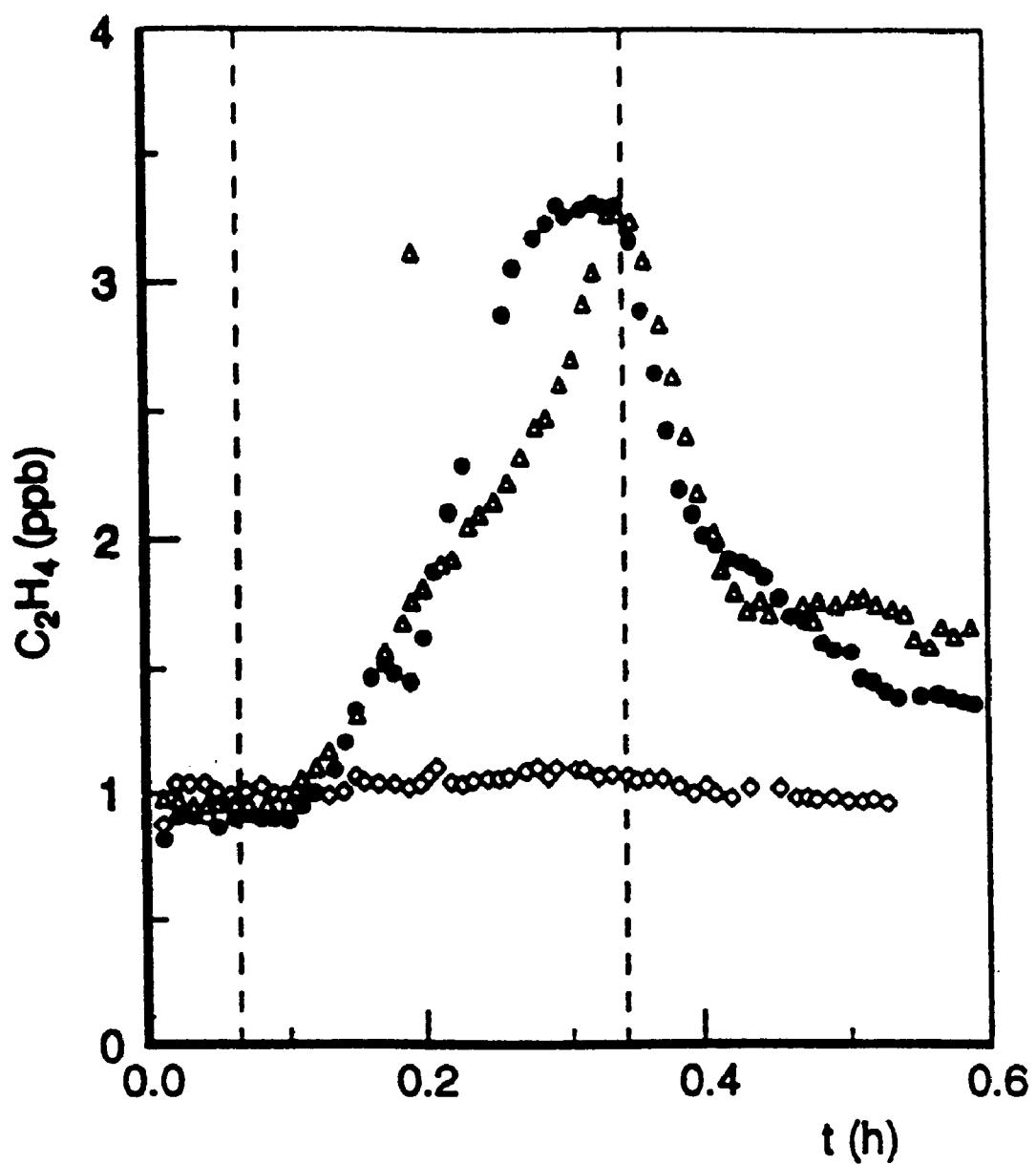

The present invention will now be explained with reference to an exemplary embodiment and with reference to the drawing in which FIG. 1 schematically shows a photoacoustic device suitable for measuring low concentrations of a compound;

FIG. 2 is a schematic representation of a device for taking samples from air exhaled by a mammal; and FIG. 3 is a graph of the measurement of ethene given off by a person on a sunbed.

The photoacoustic device shown in FIG. 1 comprises a $CO_2$ laser with a $CO_2$ discharge tube 1 and a grating 2 for adjusting the $CO_2$ laser to a suitable wavelength. A suitable wavelength is understood to be a wavelength at which, in comparison with other compounds, the compound to be measured exhibits strong absorbtion. The device further comprises a light modulator 3 ("chopper") for the periodic interruption of laser light coming from the $CO_2$ discharge tube 1, which interruption frequency F is kept very constant. For the performance of the measurement a measuring cell 4 is provided with a gas inlet 5 and a gas outlet 6. The measuring cell 4 has resonance cavity 7, and the frequency F is adjusted to the length of said resonant cavity 7. The frequency F depends on the total gas composition, the temperature and the pressure, and it will be simple for an expert to select a frequency F at which a microphone 8 measures a maximal signal. Placing the measuring cell 4 between a substantially reflecting mirror 9 and the grating 2, i.e. in the laser cavity provides a very sensitive measuring arrangement. The arrangement which is here briefly described is well-known in the field (ref. 3).

FIG. 2 is a schematic representation of a device for taking samples from air exhaled by a mammal. This device comprises a gas bottle 10 filled with compressed inhalation air. Via a reducing valve (not shown) the inhalation air is fed into a pipe 11 at a constant flow rate. The pipe 11 is in communication with a 60-liter buffer sack 12 made from a flexible plastic. Ensuring that the buffer sack 12 is partly but not completely filled, allows the mammal to breathe inhalation air at atmospheric pressure. The buffer sack 12 itself must not give off any gasses which might interfere with the measurements, and is, for instance, an aluminium-comprising plastic sack (Tecobag, Tesseraux, Bürstadt, Germany). The pipe 11 is further provided with a pressure relieve valve 13 to ensure that the mammal is never provided with air of too high a pressure, in order to prevent harmful effects on the lungs.

Via a one-way valve 14 inhalation air can reach the mouthpiece 15 and be inhaled by the mammal. Air exhaled by the mammal flows via the mouthpiece 15 and a one-way valve 16 to an approximately 2-meter long pipe 17, which is closed at the end by means of an overpressure valve 18 which ensures that no ambient air enters the device. The overpressure valve 18 already opens at slight overpressure and the major part of the air that is not used for measurement escapes via this route. The diameter of the pipes 11 and 17 is such that the mammal's breathing will not be hindered by resistance in the pipes. Pipes suitably have a diameter of 2.5 cm.

In order to measure the exhaled alveolar air, sampling should take place directly after the one-way valve 16. The air is immediately dried with the aid of a Nafion® air drier 19 (Perma Pure inc., Toms River, N.J., USA) which, with the aid of a selectively permeable membrane removes a large part of the water from the alveolar air. A membrane pump 20 raises the pressure of the predried alveolar air to an overpressure of 1 atmosphere. This overpressure is necessary for the further purification of the alveolar air.

To purify the alveolar air to be measured, it is freed of any interfering gasses. First the $CO_2$ concentration is reduced with the aid of a gas purifier 21 filled with soda lime granules. For obtaining an even lower $CO_2$ concentration, a gas purifier 22 is filled with moist potassium hydroxide. Water that has been carried along from gas purifier 22, is removed by gas purifier 23 which is filled with calcium chloride granules.

For measuring ethene in the photoacoustic measuring cell 4, pressure fluctuations caused by the membrane pump 20 have to be suppressed with the aid of a small buffer chamber 24 (volume 150 ml). The use of an electronic flow regulator 25 ensures a constant air-flow rate of, for example, 3 liters per hour. The thus treated alveolar air is finally led over a cold trap 26 cooled with liquid nitrogen, ensuring that the temperature does not drop below −150° C. because, in contrast with other interfering gas components such as, for example, ethanol and acetone, the gas that is to be measured, ethene, must not be trapped. The alveolar air is now ready for measuring and is led through the photoacoustic measuring cell 4. To check for leakages, a flow rate meter 27 is placed after the photoacoustic measuring cell 4.

By way of experiment, the effect of UV radiation on the ethene concentration in exhaled air has been examined. A testee took a seat on a sunbed. The vertical dotted line on the left in FIG. 3 indicates the time (at t=0) at the moment of switching on the sunbed at which the air after all the pretreatments, has reached the measuring cell 4 ready to be measured. The values at the left of the dotted line on the left give the ethene concentrations measured in the absence of UV radiation.

After 15 minutes the sunbed was switched off. The dotted vertical line at the right indicates the moment at which the exhaled air at the instant of switching off reaches the measuring cell.

The exhaled ethene concentration is shown to increase from 1 to 3 ppb (Δ). The application of suntan agent with a protection factor 10 was shown to have an adverse effect (●). Screening the testee from UV radiation by means of Lexan® while being subjected to the same amount of light and heat, showed that the effect of UV was measured (◊). It may be deduced from this experiment, that a suntan agent does not necessarily protect the skin against all harmful effects from UV.

After perusal of the present specification it will be obvious to the expert that the method according to the invention can be used for various applications. It is, for example, possible to monitor the progress of psoriasis in patients suffering from this skin disease and to measure the effect of treatment.

The invention also relates to a method of developing a safer sunbed, characterized in that a volatile organic compound in a gas given off by a mammal is measured using a photoacoustic spectroscopy and the mammal is subjected to UV radiation.

REFERENCES

1. Breath Tests in Medicine. Phillips, M. Scientific American, July, pp. 52–57 (1992).
2. The potential of the hydrocarbon breath test as a measure of lipid peroxidation. Kneepkens, C. M. F. et al. Free Radial Biology & Medicine, 17, No. 2, pp. 127–160 (1994).
3. Geometrical optimization of a longitudinal resonant photoacoustic cell for sensitive and fast trace gas detection. Bijnen, F. G. C. et al. Review Scientific Instruments 67(8), pp. 2914–2923 (1996).

What is claimed is:

1. A method of measuring the effect of a compound on a mammal, the method comprising measuring the concentration of an organic compound spectroscopically wherein the organic compound is a volatile organic compound, the concentration of which is measured in a gas given off by a mammal using photoacoustic spectroscopy, the volatile organic compound not being the compound or a degradation product thereof.

2. A method according to claim 1 wherein the mammal is subjected to a factor that changes the concentration of the volatile organic compound in the breath.

3. A method according to claim 2 wherein the factor is a stress factor.

4. A method according to claim 1 wherein the compound is one to be tested for the presence of a pharmaceutical characteristic.

5. A method according to claim 1 wherein the measured concentration is normalized.

6. A method according to claim 5 wherein normalization is done by using at least one parameter selected from the group consisting of weight, lung capacity (measure of lung surface area), respiratory volume (l/min), volume of each breath, blood flow rate, the concentration of a further compound selected from the group comprising a marker gas, carbon dioxide, oxygen, and the mammal's percentage of fat.

7. A method according to claim 1 wherein the volatile organic compound is a hydrocarbon composition with the general formula $C_xH_y$, x and y being integers, $x \leq 10$ and $y \geq x$.

8. A method according to claim 7 wherein the hydrocarbon compound is an unsaturated hydrocarbon compound.

9. A method according to claim 8 wherein the unsaturated hydrocarbon compound is ethene.

10. A method according to claim 1 wherein a housing which is open at one side and provided with an inlet for a carrier gas, is placed against a portion of a mammal's surface, said portion not comprising an open body orifice, the carrier gas is fed through the housing, and the carrier gas containing the gas given off by the mammal is lead away via an outlet in the housing and is subsequently measured photoacoustically.

11. A method of developing a safer sunbed, the method comprising subjecting a mammal to UV radiation, measuring a volatile organic compound in a gas given off by the mammal using photoacoustic spectroscopy when the mammal is subjected to UV radiation, and altering characteristics of the sunbed based upon results of the measuring step.

12. A method of measuring the effect of ultraviolet radiation on a mammal, the method comprising measuring the concentration of an organic compound spectroscopically wherein the organic compound is a volatile organic compound, the concentration of which is measured in a gas given off by a mammal using photoacoustic spectroscopy.

13. A method according to claim 12 wherein the measured concentration is normalized.

14. A method according to claim 13 wherein normalization is done by using at least one parameter selected from the group consisting of weight, lung capacity (measure of lung surface area), respiratory volume (l/min), volume of each breath, blood flow rate, the concentration of a compound selected from the group comprising a marker gas, carbon dioxide, oxygen, and the mammal's percentage of fat.

15. A method according to claim 12 wherein the volatile organic compound is a hydrocarbon composition with the general formula $C_xH_y$, x and y being integers, $x \leq 10$ and $y \geq x$.

16. A method according to claim 15 wherein the hydrocarbon compound is an unsaturated hydrocarbon compound.

17. A method according to claim 16 wherein the unsaturated hydrocarbon compound is ethene.

18. A method according to claim 12 wherein a housing which is open at one side and provided with an inlet for a carrier gas, is placed against a portion of a mammal's surface, said portion not comprising an open body orifice, the carrier gas is fed through the housing, and the carrier gas containing the gas given off by the mammal is lead away via an outlet in the housing and is subsequently measured photoacoustically.

\* \* \* \* \*